United States Patent
Fremy et al.

(10) Patent No.: US 8,791,314 B2
(45) Date of Patent: Jul. 29, 2014

(54) ADDITIVE FOR REDUCING COKING AND/OR CARBON MONOXIDE IN CRACKING REACTORS AND HEAT EXHANGERS AND USE OF SAME

(75) Inventors: Georges Fremy, Sauveterre de Bearn (FR); Francis Humblot, Lanneplaa (FR); Paul-Guillaume Schmitt, Billere (FR)

(73) Assignee: Arkema France, Colombes (FR)

( * ) Notice: Subject to any disclaimer, the term of this patent is extended or adjusted under 35 U.S.C. 154(b) by 405 days.

(21) Appl. No.: 12/526,317

(22) PCT Filed: Feb. 20, 2008

(86) PCT No.: PCT/FR2008/050281
§ 371 (c)(1),
(2), (4) Date: Sep. 16, 2009

(87) PCT Pub. No.: WO2008/107622
PCT Pub. Date: Sep. 12, 2008

(65) Prior Publication Data
US 2010/0069695 A1 Mar. 18, 2010

Related U.S. Application Data

(60) Provisional application No. 60/949,266, filed on Jul. 12, 2007.

(30) Foreign Application Priority Data

Feb. 20, 2007 (FR) ...................................... 07 53380

(51) Int. Cl.
*C07C 4/04* (2006.01)

(52) U.S. Cl.
USPC ........... 585/650; 585/648; 585/649; 585/652; 585/651; 585/653; 208/48 R

(58) Field of Classification Search
USPC ................ 585/648, 649, 650, 651, 652, 653; 208/48 R
See application file for complete search history.

(56) References Cited

U.S. PATENT DOCUMENTS

| | | |
|---|---|---|
| 4,116,812 A | 9/1978 | Godar et al. |
| 4,507,196 A | 3/1985 | Reed et al. |
| 4,511,405 A | 4/1985 | Reed et al. |
| 4,552,643 A | 11/1985 | Porter et al. |
| 4,613,372 A | 9/1986 | Porter et al. |
| 4,666,583 A | 5/1987 | Porter et al. |
| 4,686,201 A | 8/1987 | Porter et al. |
| 4,687,567 A | 8/1987 | Porter et al. |
| 4,804,487 A | 2/1989 | Reed et al. |
| 5,015,358 A | 5/1991 | Reed et al. |
| 5,463,159 A | 10/1995 | Callejas et al. |
| 5,616,236 A | 4/1997 | Brown et al. |
| 5,954,943 A * | 9/1999 | Tong et al. .................... 585/648 |
| 2002/0029514 A1* | 3/2002 | Lindstrom ...................... 44/640 |

FOREIGN PATENT DOCUMENTS

| | | |
|---|---|---|
| DE | 1234205 | 8/1964 |
| EP | 0333554 | 9/1989 |
| EP | 976762 | 2/2000 |
| GB | 1090983 | 11/1967 |
| WO | WO 01/96499 | 12/2001 |
| WO | WO 2005/111175 | 11/2005 |

* cited by examiner

*Primary Examiner* — In Suk Bullock
*Assistant Examiner* — Sharon Pregler
(74) *Attorney, Agent, or Firm* — RatnerPrestia

(57) ABSTRACT

The present invention concerns an additive for reducing the formation of coke and/or carbon monoxide in thermal hydrocarbon cracking units and/or of other organic compounds in heat exchangers. The additive according to the invention is essentially composed of diethyl disulphide (DEDS) or dipropyl disulphide(s) (DPDS) or dibutyl disulphide(s) (DBDS) and can be used on the metal walls of a cracking reactor and on the metal walls of a heat exchanger placed downstream from the cracking reactor, and during the process of cracking hydrocarbons and/or other organic compounds.

18 Claims, No Drawings

ADDITIVE FOR REDUCING COKING AND/OR CARBON MONOXIDE IN CRACKING REACTORS AND HEAT EXHANGERS AND USE OF SAME

FIELD OF THE INVENTION

The present invention relates to the field of the cracking of hydrocarbons or other organic compounds and has more particularly as subject-matter, a process for reducing coking on the walls of cracking reactors and heat exchangers used to cool the compounds resulting from the cracking reaction.

BACKGROUND OF THE INVENTION

In order to produce ethylene and other short-chain olefins, some hydrocarbon oil fractions are cracked thermally in tubular metal reactors. The resulting cracked gases are suddenly cooled in heat exchangers which operate by supplying water and steam under pressure.

The tubular reactors used are preferably manufactured from chromium- and nickel-rich steels, while the heat exchangers, which are subjected to less obvious stresses, are composed of carbon steels or weakly alloyed steels. This same type of equipment is also encountered in producing other organic compounds, such as vinyl chloride by pyrolysis of 1,2-dichloroethane.

The effectiveness of these reactors and heat exchangers made of steel depends on their resistance to the formation of a deposit of coke on their internal walls in contact with the hydrocarbon to be cracked. Not only is this deposit harmful to heat transfer but it reduces the effective cross section of the tube. The thickness of this coke deposit becomes such that the unit has to be halted and subjected to expensive cleaning operations. In the majority of cases, the coke deposit is removed by high-temperature gasification with a mixture of steam and air which converts the coke to carbon oxides and re-establishes the starting characteristics of the cracking tube. When the deposit is produced in the heat exchangers, it is not possible structurally to carry out an in-line decoking by gasification as the maximum temperatures acceptable are too low to allow this reaction. Dismantling and manual decoking are necessary, which is a difficult and expensive operation.

Hydrocarbon cracking units, such as steam crackers, are thus frequently shut down in order to be subjected to decoking cycles (after operating for 20 to 60 days). Furthermore, the oxidizing decoking treatment results in an increase in the catalytic activity of the metal cracking surface, which increases the rate of formation of coke. Thus, with the increase in the number of decokings undergone by the unit, the operating time decreases and the annual number of decoking operations increases. This long-term effect is injurious technically and economically since the maintenance costs become more and more burdensome with the age of the unit for a lower annual operating rate.

This is the reason why numerous efforts have been made for many years to find solutions which prevent the rapid coking of the internal metal walls of such units (cracking tubes and heat exchangers).

It is standard practice in the industrial production of ethylene to inject, with the hydrocarbon feedstock, relatively small amounts of sulphur-comprising products, such as dimethyl sulphide (DMS) or dimethyl disulphide (DMDS), in order to reduce the formation of coke. It is commonly accepted by the person skilled in the art that the sulphur passivates the active metal sites of the surface of the steam cracking tubes which are known to catalyze the formation of coke. Moreover, these sulphur-comprising compounds are known to also reduce the formation of carbon monoxide (CO) formed by the reaction of hydrocarbons or coke with steam, by passivating in the same way the active metal sites of the surface of the tubes. In fact, it is also important to minimize the amounts of CO produced in order to ensure correct operation of the separation and purification units downstream of the steam cracker.

These technical solutions and many others are described in the literature; mention may more particularly be made of the following:

U.S. Pat. No. 4,116,812 describes a process for inhibiting coke using organosulphur additives of dithiolthione type at temperatures of 260 and 815° C.

U.S. Pat. No. 5,463,159 describes a method for treating the furnaces used in the production of ethylene with compounds which generate hydrogen sulphide ($H_2S$) in order to reduce the formation of coke. The preferred $H_2S$-generating compound is dimethyl sulphide (DMS).

U.S. Pat. No. 5,616,236 discloses a method for inhibiting coke and CO by treatment of the tubes of the steam cracker with sulphur-comprising compounds in the presence of hydrogen, the sulphur-comprising compounds being of sulphide or disulphide type, DMS and DMDS being particularly preferred.

U.S. Pat. No. 5,954,943 describes a method for reducing the deposition of coke in cracking furnaces using a mixture of sulphur-comprising and phosphorus-comprising compounds with an S/O molar ratio of greater than or equal to 5.

EP 976 726 A1, which is concerned with DMDS possessing a masked odour, indicates in [0002] that it can be used as additive for charging to a steam cracker.

WO 2005/111175 describes a process for thermal cracking of hydrocarbon compounds and the use in the mixture as coke inhibitor of a mixture of organic disulphides with a carbon number of between 2 and 4 known as sulphur oil or disulphide oil (DSO). The preferred mixture is a mixture of alkyl disulphides where the alkyl groups are methyl and ethyl and where the typical sulphur content is 60%.

Coke inhibitors other than sulphur-comprising compounds are also known. Mention may be made for example of U.S. Pat. Nos. 4,507,196, 4,511,405, 4,552,643, 4,613,372, 4,666, 583, 4,686,201, 4,687,567, 4,804,487 and 5,015,358, which teach that the metals Sn, Ti, Sb, Ga, Ge, Si, In, Al, Cu, P and Cr, and their organic and inorganic derivatives, individually or as a mixture, act as coke inhibitors during the pyrolysis of the hydrocarbons.

DETAILED DESCRIPTION OF THE INVENTION

The present invention relates to novel additives which make it possible to reduce the formation of coke and/or carbon monoxide in thermal cracking units and heat exchangers which essentially comprise diethyl disulphide (DEDS) or dipropyl disulphide(s) (DPDS) or dibutyl disulphide(s) (DBDS).

According to a preferred form of the invention, the coke inhibitor and/or CO inhibitor essentially comprises DEDS.

According to a preferred form of the invention, the coke inhibitor and/or CO inhibitor essentially comprises DPDS.

According to a preferred form of the invention, the coke inhibitor and/or CO inhibitor essentially comprises DBDS.

Within the meaning of the present invention, the expression "essentially comprises" means comprises less than 20 000 ppm of impurities, preferably less than 10 000 ppm of impurities and advantageously less than 5000 ppm of impurities. The term "impurities" is understood to mean traces of one or more organosulphur compounds which can be represented by the formula RS$_n$R' with n representing the mean sulphur number ranging from 1 to 10 and R and R' representing H or a linear or branched C$_1$-C$_{24}$ alkyl, cycloalkyl or aryl chain, such as, for example, DMDS, dimethyl sulphide, methyl mercaptan, ethyl mercaptan, DPDS and/or DBDS, when the coke and CO inhibitor essentially comprises DEDS.

The terms "dipropyl disulphide(s) (DPDS)" and "dibutyl disulphide(s) (DBDS)" are understood to mean the isomer or isomers of dipropyl disulphide and dibutyl disulphide, respectively, for example n-propyl and/or isopropyl disulphide or n-butyl, isobutyl and/or tert-butyl disulphide.

These novel additives exhibit advantages not only with respect to DMDS, the reference coke and/or CO inhibitor in the industry, but also with respect to the mixtures of disulphides described in the prior art. This is because DMDS and the mixtures of dialkyl disulphides of the prior art, for example dimethyl disulphide and diethyl disulphide mixtures, exhibit the disadvantage of thermally decomposing largely to give methane, which is found in the final product. In point of fact, producers of olefins are interested in maximizing the yield of olefins, more particularly of ethylene, propylene and butene. The coke and/or CO inhibitors according to the invention, which make it possible, by their thermal decomposition, to increase the yield of olefins in the final product, are particularly advantageous for manufacturers insofar as their decomposition makes it possible to produce olefins, such as ethylene, propylene and butene, respectively, thus increasing the yield of olefins in the final product at the outlet of the cracking furnace.

The second subject-matter of the invention is a process for reducing coking and/or carbon monoxide on the metal walls of a reactor for the cracking of hydrocarbons and/or other organic compounds and on the metal walls of a heat exchanger placed subsequent to the cracking reactor, characterized in that the metal surfaces coming into contact with the organic substance to be cracked are pretreated with a stream of steam comprising in particular the additive according to the invention, at a temperature of between 300 and 1100° C., preferably between 400 and 700° C. for the heat exchanger and preferably between 750 and 1050° C. for the cracking tube, for a period of time between 0.5 and 12 hours, preferably between 1 and 6 hours.

The concentration of the additive according to the invention in the carrier fluid composed of steam alone or mixed with an inert gas (nitrogen, hydrogen, methane and/or ethane and the like) can generally range from 50 to 5000 ppm by weight. Preferably this concentration is between 100 and 3000 ppm by weight.

The pressure of the carrier fluid is generally equal to that employed conventionally in cracking furnaces (between 1 and 20 bar absolute, advantageously between 1 and 5 bar absolute).

The pre-treatment according to the invention can be carried out in any new cracking unit or in any existing unit after each decoking operation. It is particularly easy to install in steam cracking units since it uses steam as carrier gas, a fluid already normally available in the said units.

A third subject-matter of the invention is also a process for the cracking of hydrocarbons and/or other organic compounds in which the additive according to the invention is added during the cracking with the feedstock of organic compounds, which cracking is generally carried out between 600 and 1000° C., preferably between 650 and 900° C. This addition can be carried out at a lower temperature, to the liquid feedstock, before it is preheated and evaporated and/or during the preheating phase, up to 600° C. When the cracking is carried out in the presence of steam, this addition can be carried out into the steam, between 150 and 650° C.

The concentration of additive according to the invention is chosen so that the concentration of sulphur in the hydrocarbons and/or organic compounds to be cracked is preferably between 10 and 1000 ppm by weight and advantageously between 20 and 400 ppm by weight.

The following example illustrates the invention without limiting it.

EXAMPLE

In this example the thermal decomposition of several additives either according to the invention or known to a person skilled in the art, is tested. This example makes it possible to compare the sulphur-comprising agents of the present invention with sulphur-comprising agents known to a person skilled in the art or described in the prior art: DEDS (additive according to the invention) and by way of comparison, DMS and DMDS respectively.

Pyrolysis tests are carried out in a furnace which can range up to 1000° C., the additive being introduced with a flow rate of 0.5 ml/h and water being introduced with a flow rate of 13.5 ml/h under a hydrogen stream of 40 l/h. The residence time is approximately 0.5 s.

On exiting from the furnace, the gases are analyzed by chromatography.

In this example, the aspect concerned will be the percentages by weight of hydrocarbons formed with respect to the total weight of hydrocarbons generated during the heat treatment.

The percentages by weight of hydrocarbons (methane (CH$_4$), ethane (C$_2$H$_6$) and ethylene (C$_2$H$_4$)) with respect to the total weight of hydrocarbons obtained by thermal decomposition of each of the additives tested at a temperature of 800° C., a value typical in steam cracking units, are shown in the table below.

| Additive tested | CH$_4$ (%) | C$_2$H$_6$ (%) | C$_2$H$_4$ (%) |
|---|---|---|---|
| DMDS | 77.2 | 5.2 | 17.6 |
| DMS | 89.3 | 2.2 | 8.5 |
| DEDS | 2.5 | 20.3 | 77.2 |

The advantage of using DEDS in comparison with DMDS or DMS is clearly seen as, on decomposing, it forms much more ethylene and thus makes it possible to increase the yield of the industrial unit.

The invention claimed is:

1. Process for reducing coking and/or carbon monoxide formation on metal walls of a reactor and/or heat exchanger used for cracking of hydrocarbons and/or other organic compounds to produce olefins, characterized in pretreating the metal walls with a stream comprising a carrier fluid and an additive selected from the group consisting of diethyl disulphide (DEDS), dipropyl disulphide (DPDS) and dibutyl disulphide (DBDS), at a temperature of between 300 and 1100° C. for a period of time between 0.5 and 12 hours said stream containing less than 20,000 ppm of impurities with respect to the total amount of the additive wherein the impurities are selected from the group consisting of dimethyl disulphide, dimethyl sulphide, methyl mercaptan and ethyl mercaptan.

2. Process according to claim 1, in which the pretreating is carried out at a temperature of between 750 and 1050° C.

3. Process according to claim 1, in which the pretreating is carried out for a period of time of 1 to 6 hours.

4. Process according to claim 1, in which the carrier fluid is steam.

5. Process according to claim 4, in which the carrier fluid further comprises an inert gas.

6. Process according to claim 1, in which the pretreating is at a pressure of between 1 and 20 bar absolute.

7. Process according to claim 1, characterized in that the concentration of additive in the carrier fluid is between 50 and 5000 ppm by weight.

8. Process for reducing coking and/or carbon monoxide formation during the cracking of hydrocarbons and/or other organic compounds to produce olefins, characterized in that a stream comprising a carrier fluid and a sulphur containing additive selected from the group consisting of diethyl disulphide (DEDS), dipropyl disulphide (DPDS) and dibutyl disulphide (DBDS), is added to a feedstock of hydrocarbons and/or organic compounds before the feedstock is preheated and evaporated and/or during preheating the feedstock said stream containing less than 20,000 ppm of impurities with respect to the total amount of the sulphur containing additive, wherein the impurities are selected from the group consisting of dimethyl disulfide, dimethyl sulphide, methyl mercaptan and ethyl mercaptan.

9. Process according to claim 8, characterized in that the cracking temperature is between 600 and 1000° C.

10. Process according to claim 8 characterized in that the cracking temperature is between 150 and 650° C.

11. Process according to claim 8, characterized in that the concentration of additive is such that the concentration of sulphur in the hydrocarbons and/or organic compounds to be cracked is between 10 and 1000 ppm by weight.

12. Process according to claim 1, in which the pretreating is carried out at a temperature of between 400 and 700° C.

13. Process according to claim 5, in which the inert gas is selected from the group consisting of nitrogen, hydrogen, methane, ethane and mixtures thereof.

14. Process according to claim 1, in which the pretreating is at a pressure of between 1 and 5 bar absolute.

15. Process according to claim 1, characterized in that the concentration of additive in the carrier fluid is between 100 and 3000 ppm.

16. Process according to claim 8, characterized in that the cracking temperature is between 650 and 900° C.

17. Process according to claim 8, in which the carrier fluid is steam.

18. Process according to claim 8, characterized in that the concentration of additive is such that the concentration of sulphur in the hydrocarbons and/or organic compounds to be cracked is between 20 and 400 ppm by weight.

* * * * *